US011538577B2

(12) United States Patent
Rahman et al.

(10) Patent No.: US 11,538,577 B2
(45) Date of Patent: Dec. 27, 2022

(54) SYSTEM AND METHOD FOR AUTOMATED DIAGNOSIS OF SKIN CANCER TYPES FROM DERMOSCOPIC IMAGES

(71) Applicant: Morgan State University, Baltimore, MD (US)

(72) Inventors: Md Mahmudur Rahman, Baltimore, MD (US); Oyebisi Francis Layode, Bowie, MD (US); Tasmeer Alam, Baltimore, MD (US)

(73) Assignee: Morgan State University, Baltimore, MD (US)

( * ) Notice: Subject to any disclaimer, the term of this patent is extended or adjusted under 35 U.S.C. 154(b) by 51 days.

(21) Appl. No.: 17/075,850

(22) Filed: Oct. 21, 2020

(65) Prior Publication Data
US 2021/0118550 A1 Apr. 22, 2021

Related U.S. Application Data

(60) Provisional application No. 62/923,793, filed on Oct. 21, 2019.

(51) Int. Cl.
*G06K 9/00* (2022.01)
*G16H 30/40* (2018.01)
(Continued)

(52) U.S. Cl.
CPC ........... *G16H 30/40* (2018.01); *G06F 16/538* (2019.01); *G06N 3/08* (2013.01); *G06N 20/10* (2019.01);
(Continued)

(58) Field of Classification Search
CPC ........ G16H 30/40; G16H 50/20; G16H 50/70; G06F 16/538; G06F 16/583; G06N 3/08;
(Continued)

(56) References Cited

U.S. PATENT DOCUMENTS

| 7,415,143 B2 | 8/2008 | Grichnik |
| 7,689,016 B2 | 3/2010 | Stoecker et al. |

(Continued)

FOREIGN PATENT DOCUMENTS

| CN | 108778097 A | * | 11/2018 | ........... A61B 5/0002 |
| CN | 109923581 A | * | 6/2019 | ........... A61B 5/1171 |

OTHER PUBLICATIONS

M. E. Celebi, H. A. Kingravi, B. Uddin, H. Iyatomi, Y. A. Aslandogan, W. V. Stoecker, and R. H. Mosse, A Methodological approach to the classification of dermoscopy images, Computerized Medical Imaging and Graphics, 2007, 31, 362-373.

(Continued)

*Primary Examiner* — Xin Jia
(74) *Attorney, Agent, or Firm* — Whiteford, Taylor & Preston, LLP; Gregory M. Stone

(57) ABSTRACT

Disclosed is a content-based image retrieval (CBIR) system and related methods that serve as a diagnostic aid for diagnosing whether a dermoscopic image correlates to a skin cancer type. Systems and methods according to aspects of the invention use as a reference a set of images of pathologically confirmed benign or malignant past cases from a collection of different classes that are of high similarity to the unknown new case in question, along with their diagnostic profiles. Systems and methods according to aspects of the invention predict what class of skin cancer is associated with a particular patient skin lesion, and may be employed as a diagnostic aid for general practitioners and dermatologists.

20 Claims, 5 Drawing Sheets

(51) Int. Cl.
*G16H 50/20* (2018.01)
*G06T 7/00* (2017.01)
*G06N 3/08* (2006.01)
*G06N 20/10* (2019.01)
*G06F 16/538* (2019.01)

(52) U.S. Cl.
CPC ........... *G06T 7/0012* (2013.01); *G16H 50/20* (2018.01); *G06T 2207/20084* (2013.01); *G06T 2207/30096* (2013.01)

(58) Field of Classification Search
CPC ...... G06N 20/10; G06N 3/0454; G06N 20/00; G06T 7/0012; G06T 2207/20084; G06T 2207/30096; G06T 2207/30088; G06T 7/0014; G06V 30/2528; G06V 2201/03; G06V 10/75; G06K 9/629; G06K 9/6292
See application file for complete search history.

(56) References Cited

U.S. PATENT DOCUMENTS

| | | | |
|---|---|---|---|
| 9,595,084 | B2 | 3/2017 | Houjou et al. |
| 9,858,666 | B2 | 1/2018 | Houjou et al. |
| 10,223,788 | B2 | 3/2019 | Bozorgtabar et al. |
| 2010/0302358 | A1* | 12/2010 | Chen ................. A61B 5/7282 600/407 |
| 2018/0061051 | A1* | 3/2018 | Matsunaga ............ A61B 5/444 |
| 2022/0020494 | A1* | 1/2022 | Shin ....................... G16H 30/40 |

OTHER PUBLICATIONS

H. Ganster, A. Pinz, R. Rohrer, E. Wildling, M. Binder, and H. Kittier, Automated Melanoma Recognition, IEEE Trans. Medical Imaging, 2001, 20(3), 233-239.
P. S. Saugeon, J. Guillod, J Thiran, Towards a computer-aided diagnosis system for pigmented skin lesions, Computerized Medical Imaging and Graphics, 2003, 27, 65-78.
M. Rahman, B. C. Desai, and P. Bhattacharya, Image Retrieval-Based Decision Support System for Dermatoscopic mages, 2006, IEEE Symposium on Computer-Based Medical Systems (CBMS'06).
B. Alfonso, M. Raffaele, D. Emanuele, M. Mario, G. Oscar, B. Stefano, and G. Luca, Definition of an automated Content-Based Image Retrieval (CBIR) system for the comparison of dermoscopic images of pigmented skin lesions, BioMedical Engineering OnLine, 2009, 8(18), doi:10.1186/1475-925X-8-18.
B. Lucia, L. Xiang, B. F. Robert, A. Ben, R. Jonathan, Content-Based Image Retrieval of Skin Lesions by Evolutionary Feature Synthesis, Applications of Evolutionary Computation, Lecture Notes in Computer Science, 2010, 6024, 312-319.
T. J. Brinker, A Hekler, J. S. Utikal, N. Grabe, D. Schadendorf, J. Klode et al., Skin cancer classification using convolutional neural networks: systematic review. J Med Internet Res. 2018; 20: e11936.
A. Esteva, B. Kuprel, R. A. Novoa, J. Ko, S. M. Swetter, H. M. Blau and S. Thrun, Dermatologist-level classification of skin cancer with deep neural networks, Nature vol. 542, pp. 115-118, Feb. 2, 2017.
M. A. Marchetti, N. C. Codella, S. W. Dusza, D. A. Gutman, B. Helba, A. Kalloo et al., Results of the 2016 international skin imaging collaboration international symposium on biomedical imaging challenge: comparison of the accuracy of computer algorithms to dermatologists for the diagnosis of melanoma from dermoscopic images (e271)J Am Acad Dermatol. 2018; 78:270-277.
D. Gutman, N. C. Codella, E. Celebi, B. Helba, M. Marchetti, N. Mishra et al., Skin lesion analysis toward melanoma detection: a challenge at the international symposium on biomedical imaging (ISBI) 2016, hosted by the international skin imaging collaboration (ISIC). (arXiv preprint arXiv: 160501397); 2016.
H. Haenssle, C. Fink, R. Schneiderbauer, F. Toberer, T. Buhl, A. Blum et al., Man against machine: diagnostic performance of a deep learning convolutional neural network for dermoscopic melanoma recognition in comparison to 58 dermatologists. Ann Oncol. 2018; 29: 1836-1842.
N. Codella, J. Cai, M. Abedini, R. Garnavi, A. Halpern, and J. R. Smith, "Deep learning, sparse coding, and SVM for melanoma recognition in dermoscopy images," in MICCAI MLMI, vol. 9352, 2015, pp. 118-126.
L. Xu, M. Jackowski, A. Goshtasby, D. Roseman, S. Bines, C. Yu et al. Segmentation of skin cancer images. Image Vis Comput 1999;17:65-74.
O. Ronneberger, P. Fischer, T. Brox, U-Net: Convolutional Networks for Biomedical Image Segmentation. In: N. Navab, J. Hornegger, W. Wells, A. Frangi (eds) Medical Image Computing and Computer-Assisted Intervention—MICCAI 2015. MICCAI 2015. Lecture Notes in Computer Science, vol. 9351. Springer, Cham, (2015).

* cited by examiner

SYSTEM AND METHOD FOR AUTOMATED DIAGNOSIS OF SKIN CANCER TYPES FROM DERMOSCOPIC IMAGES

CROSS REFERENCE TO RELATED APPLICATIONS

This application is based upon and claims the benefit of U.S. Provisional Application No. 62/923,793 titled "Retrieval-Based Decision Support System to Enable the Automated Diagnosis of Multiple Skin Cancer Types from Dermoscopic Images," filed with the United States Patent & Trademark Office on Oct. 21, 2019, the specification of which is incorporated herein by reference in its entirety.

FIELD OF THE INVENTION

This invention relates generally to computer-implemented analysis of medical image data as a diagnostic aid, and more particularly to computer-implemented systems and methods for determining whether a dermoscopic image correlates to a skin cancer type by comparing a digital image of a suspected case of skin cancer against a set of digital images from one or more datasets of known cases of skin cancer.

BACKGROUND OF THE INVENTION

Skin cancer is one of the most frequent cancers among human beings, and early diagnosis of an unknown skin lesion is critical to providing treatment. However, catching a dangerous or potentially dangerous or cancerous skin lesion early enough to save a patient's life can be challenging. Classification of a particular skin lesion as potentially cancerous may require a level of skill and experience that some dermatologists might not yet have developed, and more frequently that general medical practitioners significantly lack.

As a result, certain automated tools have been developed to assist in the diagnosis of cancerous or otherwise dangerous skin lesions. For example, the rapid advancement of digital image processing and machine learning techniques have brought about computer-aided diagnosis (CAD) systems in which dermoscopic images are intended to be used to detect and screen skin cancers, and particularly melanomas, at an early stage of development. Unfortunately though, previously known CAD systems are typically non-interactive in nature, and the prediction represents just a cue for the dermatologist without the ability to explain the reasoning of the decision making, as the final decision regarding the likelihood of the presence of a cancerous lesion is left exclusively to the dermatologist. As a result, such CAD-based tools have had little practical benefit to dermatologists thus far.

Further, the descriptiveness and discriminative power of features extracted from dermoscopic images to effectively represent the structure and characteristics of lesions and effectively handle the within-class variation and between-class similarity are critical to achieving good classification and retrieval performances. In recent years, there has been a renewed interest in the field of deep learning, and the latest research in the area of medical imaging using deep learning shows promising results. Recent research in computer vision and pattern recognition has highlighted the capabilities of Convolutional Neural Networks (CNNs) to solve challenging tasks such as classification, segmentation and object detection, achieving state-of-the art performances. This success has been attributed to the ability of CNNs to learn a hierarchical representation of raw input data to capture the intrinsic image features without manual feature design. As the inputs are processed through the network layers, the level of abstraction of the resulting features increases. Shallower layers grasp local information, while deeper layers use filters whose receptive fields are much broader and therefore capture global information. Recent studies have suggested that the use of deep learning can significantly improve the performance of such CAD systems, but such methods and systems have not yet achieved widespread viability.

Various other efforts have been made to address skin lesion diagnosis through evaluation of digital images. For example, U.S. Pat. No. 7,415,143 to Grichnik discloses a method for observing and comparing uniformity and change over time of an image of a skin lesion. Further, U.S. Pat. No. 7,689,016 to Stoecker et al. discloses processing of digital images of skin lesions by using lesion segmentation to refine the image for purposes of detecting melanoma. Still further, U.S. Pat. Nos. 9,595,084 and 9,858,666 to Houjou et al. disclose a medical skin examination device and method for processing and enhancing sequential images of a skin lesion for evaluation of the progression of the lesion over time. Even further, U.S. Pat. No. 10,223,788 to Bozorgtabar et al. focusses on segmentation of a lesion image to identify pixels that are lesion and pixels that are non-lesion. However, such efforts have unfortunately not provided for sufficiently reliable and easy to use methods of diagnosing skin lesions.

Therefore, there remains a need in the art for reliable and easy to use systems and methods capable of assisting a dermatologist or other medical professional in evaluating and diagnosing skin lesions as cancerous, potentially cancerous, or otherwise dangerous to the patient.

SUMMARY OF THE INVENTION

Disclosed herein is an integrated classification and retrieval based Decision Support System (DSS) for skin cancer detection with an easy to use user interface that uses fusion and ensemble techniques in deep feature spaces. Deep features are extracted from images based on using transfer learning in several pre-trained Convolutional Neural Networks (CNNs), and Logistic Regression and Support Vector Machine (SVM) models are built as ensembles of classifiers on top of these feature vectors. Furthermore, the content-based image retrieval (CBIR) technique uses the same deep features by fusing those in different feature combinations using a canonical correlation analysis. Based on image-based visual queries submitted by dermatologists, the system responds by displaying relevant images of pigmented skin lesions of past cases, as well as classifies the image category as different types of skin cancer. An exemplary system embodying certain aspects of the invention was trained on a dermoscopic image dataset consisting of 1300 images of ten different classes. The best classification (85%) and retrieval accuracies are achieved in a test data set when feature fusion and ensemble techniques are used in all available deep feature spaces. Systems and methods accordance to aspects of the invention may reduce the visual observation error of human operators and enhance clinical decision support for early screening of skin cancers.

Systems and methods configured in accordance with certain aspects of the invention provide an interactive approach to diagnosing a skin lesion, in which the system retrieves a number of lesion images from a database of already diagnosed cases, similar to the one under analysis in addition to predicting the category of that unknown image. By providing the practitioner with a set of pathologically-confirmed past cases as computer output, the system described herein may be used to guide the practitioner to a precise diagnosis. Thus, by querying the system with a new image and consulting the retrieved images along with their tagged proven pathological diagnosis, the dermatologist can gain more confidence regarding the decision that he/she has made without consulting the CAD system, or even sometimes see the scope of considering other possibilities. Further, an integrated system based on both classification and retrieval may be more effective and robust as compared to using individual classification or retrieval approaches alone.

Systems and methods configured in accordance with certain aspects of the invention further provide a deep learning based integrated and effective DSS for skin cancer recognition via dermoscopic images. Such systems and methods work as a visual aid for the dermatologist, for example, to assist them in the diagnosis of skin cancer with statistical precision. The early diagnosis through periodic screening with dermoscopic images can significantly improve the survival rate in the clinical setting.

In accordance with certain aspects of an embodiment of the invention, an automated method for diagnosing a skin cancer type from a dermoscopic image is provided, comprising: receiving at a processor of a diagnosing system computer a digital query image of a skin lesion from an image capture device; comparing at the processor the digital query image to a plurality of digital images in a database, wherein the database comprises digital images of pathologically confirmed types of skin lesions; selecting at the processor a plurality of the pathologically confirmed digital images from the database that have a designated similarity to the digital query image; and causing the processor to display to a user probabilities that the digital query image displays a skin lesion having a pathology matching each of a plurality of skin cancer types.

In accordance with further aspects of an embodiment of the invention, a system for the automated diagnosing of a skin cancer type from a dermoscopic image is provided, comprising a memory and a processor in data communication with the memory, the memory having computer executable instructions stored thereon configured to be executed by the processor to cause the system to: receive a digital query image of a skin lesion from an image capture device; compare at the processor the digital query image to a plurality of digital images in a database, wherein the database comprises digital images of pathologically confirmed types of skin lesions; select a plurality of the pathologically confirmed digital images from the database that have a designated similarity to the digital query image; and display to a user probabilities that the digital query image displays a skin lesion having a pathology matching each of a plurality of skin cancer types.

In accordance with still further aspects of an embodiment of the invention, a non-transitory computer-readable medium is provided having stored thereon one or more code sections each comprising a plurality of instructions executable by one or more processors, the instructions configured to cause the one or more processors to perform the actions of an automated method for diagnosing a skin cancer type, the actions of the method comprising the steps of: receiving a digital query image of a skin lesion from an image capture device; comparing the digital query image to a plurality of digital images in a database, wherein the database comprises digital images of pathologically confirmed types of skin lesions; selecting a plurality of the pathologically confirmed digital images from the database that have a designated similarity to the digital query image; and displaying to a user probabilities that the digital query image displays a skin lesion having a pathology matching each of a plurality of skin cancer types.

Still other aspects, features and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The numerous advantages of the present invention may be better understood by those skilled in the art by reference to the accompanying drawings in which.

DETAILED DESCRIPTION

Figure 1:
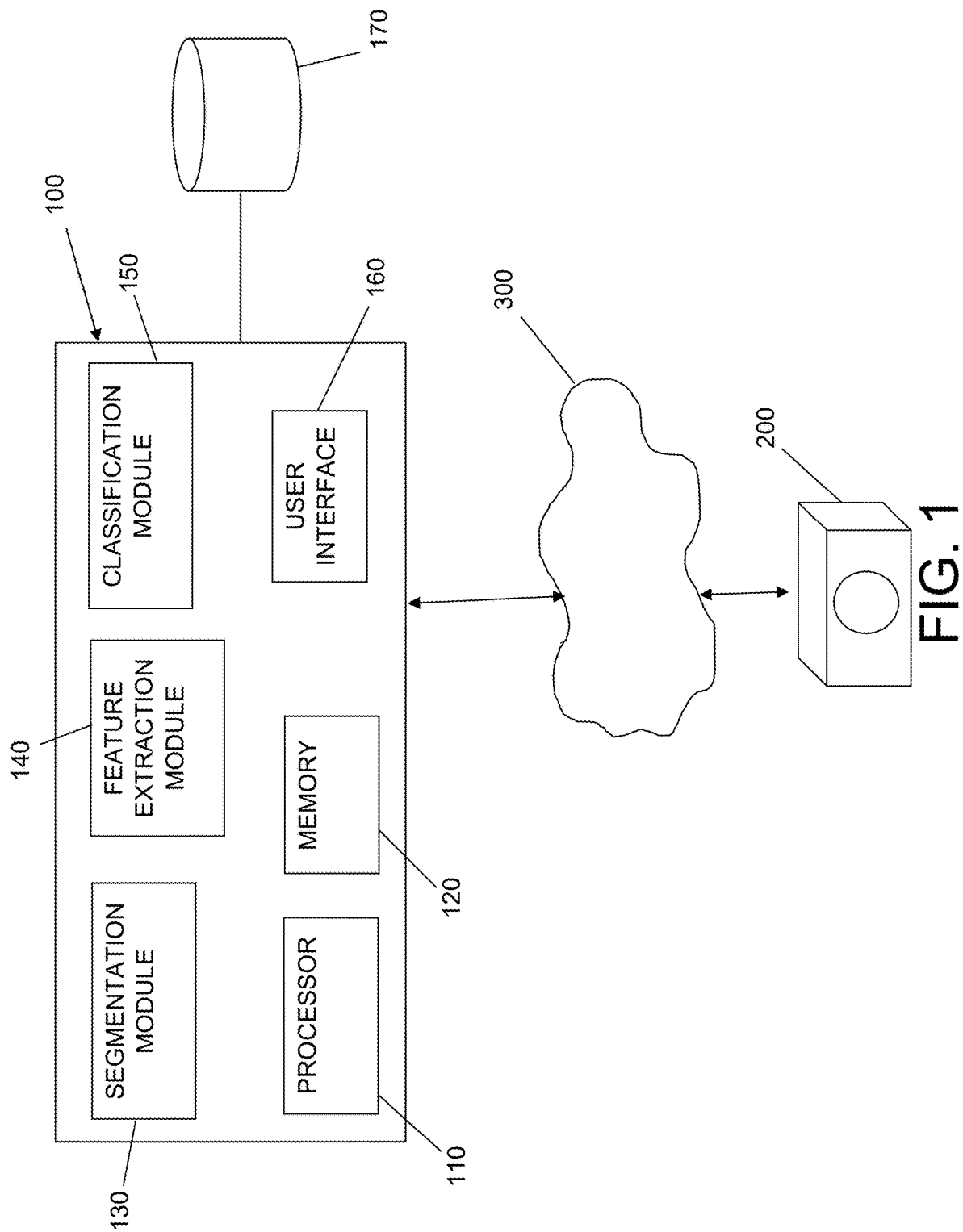
FIG. 1 provides a schematic view of a system for aiding in the diagnosis of a skin lesion through digital image processing in accordance with certain aspects of an embodiment of the invention.

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

By way of summary, systems and methods configured in accordance with certain aspects of the invention provide a content-based image retrieval (CBIR) system that serves as a diagnostic aid that provides a set of dermoscopic images of pathologically confirmed benign or malignant past cases, which are of high similarity to an unknown new case in question, along with the diagnostic profiles of the confirmed images. While such systems and methods are not intended per se as a replacement for a dermatologist by predicting the disease state of a particular case, such systems and methods may be used as a diagnostic aid for both general practitioners and less practiced dermatologists in making such diagnoses.

Systems and method configured in accordance with certain aspects of the invention may be multi-disciplinary in nature, as they may combine techniques from several fields, such as image processing, computer vision, information retrieval, deep learning and data mining. Those systems and methods for retrieving and classifying dermoscopic images may be carried out in four main stages, including (i) segmentation of the image to remove extraneous information, (ii) feature extraction from lesions, (iii) lesion classification via an ensemble method, and (iv) image retrieval by similarity matching of query and database images, all of which are discussed in detail below.

FIG. 1 provides a schematic view of a system for aiding in the diagnosis of a skin lesion through digital image processing in accordance with certain aspects of an embodiment of the invention. As shown in FIG. 1, system 100 includes a processor 110, memory 120, image segmentation module 130, feature extraction module 140, classification module 150, user interface 160, and database 170 containing pathologically confirmed skin lesion images. The functions of each of the foregoing are discussed in greater detail below. However, by way of summary, system 100 is preferably accessible via a medical practitioner, such as a dermatologist, to enable that medical practitioner to transmit a digital image of a patient's skin lesion that is captured using an image capture device 200, such as a dermascope, a digital camera, or such other digital image capture device as may be apparent to those skilled in the art, through a wide area network 300 such as the Internet, which digital image may be used by system 100 as a query image to search for similar images in database 170, and thus similar pathological diagnosis for similar skin lesions of other patients. The medical practitioner preferably engages system 100 through user interface 160 (discussed in greater detail below) and may have the option of using image segmentation module 130 to segment the image for detecting the lesion as a minimum bounding box (MBR) or use the entire image with background information. Deep features of the skin lesion in the query image are then extracted from the query image by feature extraction module 140. Next, system 100 uses classification module 150 to perform the task of classification and retrieves relevant images of past cases present in database 170. In certain optimal configurations, the medical practitioner using user interface 160 may select differing Convolutional Neural Network (CNN) selections which may be fused using a regression analysis, and an ensemble of classification models can be used for the final image classification. Further, the medical practitioner may optionally select different similarity measures and feature fusion approaches in the deep feature spaces of database and query images for both flexibility and effectiveness. Following the classification and retrieval of relevant images, such retrieved images of pathologically confirmed skin lesions that have been automatically determined as similar to the query image of the patient's skin lesion may then be transmitted through network 300 to the medical practitioner for display on their local device to aid in making a diagnosis of the patient's skin lesion.

Figure 2:
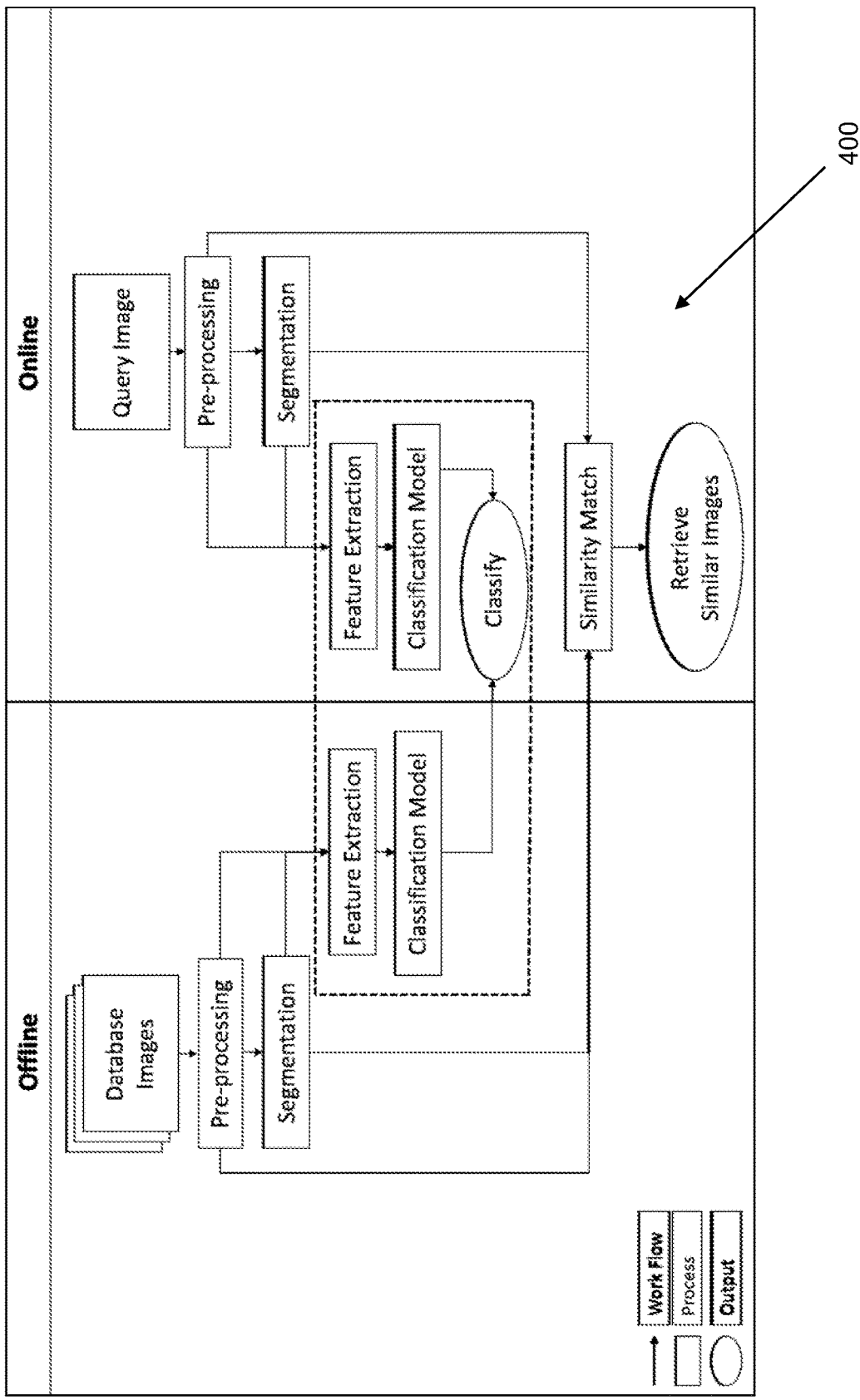
FIG. 2 is a schematic diagram of a workflow for training and classifying prior pathologically confirmed skin lesion images for use with system 100.

As shown in the schematic view of FIG. 2, database 170 of pathologically confirmed skin lesion images may be formed, maintained, and updated in a system 400 that employs both offline and online phases. During offline processing, images of skin lesions of known pathology are trained for classification and indexed in database 170. During such offline processing, system 100 may first pre-process each image that is to be included in database 170 by resizing each such image for the respective CNN approaches that are to be employed by system 100. Using the transfer learning approach, the deep features of the confirmed images are extracted by passing them through the CNNs that are without a classification head. The results obtained after this stage are the features that would have been passed to the classification layer. Classification models, such as Logistic Regression and Support Vector Machine (SVM) (the methods of which are known to those skilled in the art) are then built on top of the extracted features as these bottleneck features learned by the CNNs are quite distinct and specific to each image.

In an exemplary configuration, the images passed to the CNNs were also first segmented and the steps of training a classification model were also repeated. The extracted features may also be used for classification and retrieval using a Canonical Correlation Analysis, the method of which is known to those skilled in the art.

As mentioned above, segmentation module 130 may be used to pre-process a lesion image, employing a lesion segmentation algorithm to increase the amount of cross-section of a lesion relative to the total area of the image. Such segmentation processing is helpful to eliminate noise (i.e., skin pixels) that may impact classification accuracy. The segmentation processing involves linking each pixel of an image to a class label. The use of UNet, for example, allows for training on dermoscopic images and equivalent mask images from a dataset. A deep learning model based on UNet architecture is thus preferably employed in systems and methods configured in accordance with aspects of the invention. The UNet convolutional architecture consists of a contracting path to capture context and a symmetric expanding path that enables precise localization of pixel information. The model may be enhanced by employing a multi-stage segmentation approach with batch normalization and data augmentation. This demonstrates the segmentation of skin lesions using fully convolutional networks (FCNs) that train on a few skin lesion images from end-to-end using only the images' pixels and disease ground truth labels as inputs. The output of the segmentation model as a lesion mask may then be used for later processing steps.

In a test implementation of a system and method according to aspects of the invention, a 1000×1000 pixel image was resized (i.e., sized down) to 227×227 pixels and segmented using a deep learning model based on UNet architecture. By performing this function, better pixel analysis was enabled, which may be able to distinguish between background (normal skin) and foreground (lesion) through scoring that produces higher scores for lesions.

Generally, segmentation is not compulsory before feature extraction (discussed below), but it is preferably employed in those instances where an image needs to be denoised to obtain the lesion image necessary for feature extraction, prior to classification.

Figure 3:
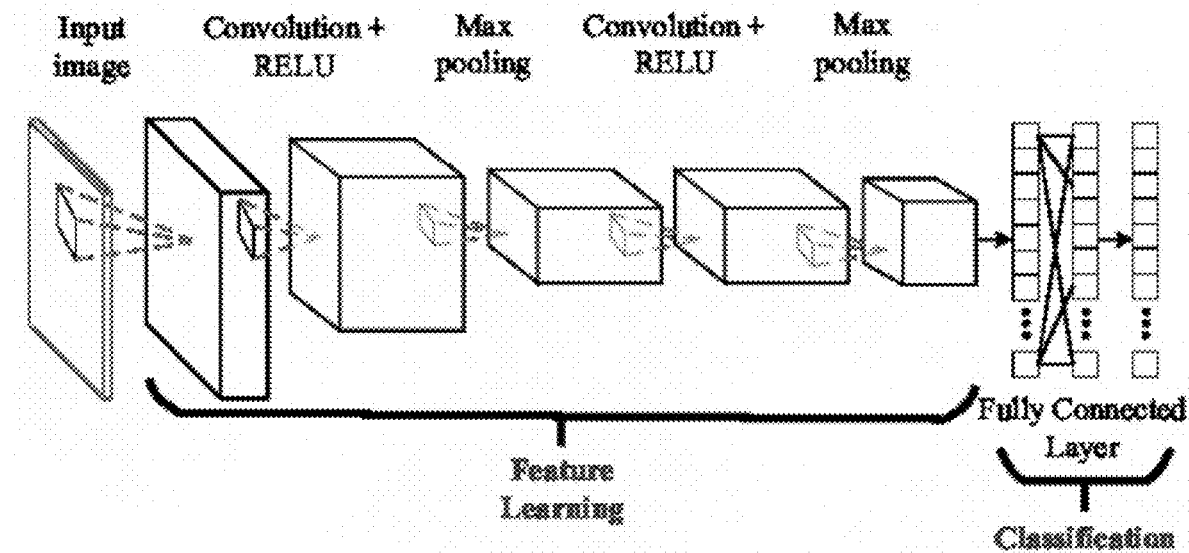
FIG. 3 is a schematic diagram of a Convolutional Neural Network (CNN) that may be implemented by a feature extraction module of the system of FIG. 1.

Next, feature extraction module 140 of system 100 may be used to extract deep features from the images by passing the images to pretrained CNN models, which as described in the following detailed discussion preferably employ ResNet, VGG, and Inception networks (the structures and methods of which are known to those skilled in the art). As shown in the schematic view of FIG. 3, and as will be apparent to those skilled in the art of CNN models, the CNN architecture of an already trained CNN model consists of a feature learning phase preceding the classification of an input image. The output of the feature learning phase is a deep feature vector that is passed to classification module 150. The output of the CNN architecture is thus the feature vector learned during the feature learning stage.

Transfer learning techniques can be used to extract features of dermoscopic images from a relatively small dataset using pretrained CNN models. Transfer learning increases the efficiency of the feature extraction process as it has been consistently proven to boost model accuracy with fewer data and reduce required training time. CNNs trained on large-scale datasets such as ImageNet have demonstrated to be excellent at the task of transfer learning. These networks learn a set of rich, discriminating features to recognize 1,000 separate object classes. Using a pretrained CNN as a feature extractor rather than training a CNN from scratch is attractive as it transfers learning (i.e., filters) from other domains where more training data is available and avoids a time consuming training process.

To perform deep feature extraction based on transfer learning, an exemplary configuration of a system and method according to the invention employed VGG-19, ResNet-50, and Inception as pre-trained CNN models on an ImageNet dataset of 1000 categories. However, these CNNs learn features that are enough to give relatively accurate classification results. VGG-19 consists of 19 fully connected convolutional layers which have been used in many machine learning applications as a baseline feature extractor. ResNet, short for Residual Networks, is another classic neural network which has been inspired by the VGG Net architecture. Typical ResNet models are implemented with double- or triple-layer skips that contain nonlinearities (ReLU) and batch normalization in between. Skipping effectively simplifies the network, using fewer layers in the initial training stages. This speeds up learning by reducing the impact of vanishing gradients, as there are fewer layers to propagate through. The network then gradually restores the skipped layers as it learns the feature space. GoogleNet or Inception v1 is basically a CNN which is 27 layers deep, and the inception layer is a combination of all layers (namely, 1×1 Convolutional layer, 3×3 Convolutional layer, 5×5 Convolutional layer) with their output filter banks concatenated into a single output vector forming the input of the next stage.

For example, when treating the VGG-19 networks as a feature extractor, we essentially "chop off" the network prior to the fully-connected layers. The last layer of the network is a max pooling layer, which will have the output shape of 7×7×512, implying that there are 512 filters each of size 7×7. If we were to forward propagate an image (pre-processed to 3 channels, 224×224 pixel) through this network with its FC head removed, we would be left with 512, 7×7 activations that have either activated or not based on the image contents.

Therefore, we may actually take these 7×7×512=25,088 values and treat them as a feature vector that quantifies the contents of an image. After repeating this process for the entire dataset of images (including datasets that VGG-19 was not trained on), we are left with a design matrix of N images, each with 25,088 columns used to quantify their contents (i.e., feature vectors). In similar fashion, ResNet-50 and Inception models can generate outputs of 5×5×2048 and 14×14×512 respectively for input image sizes of 224×224 and 299×299.

Given these deep feature vectors, we may train any off-the-shelf machine learning models, such as SVM, Logistic Regression classifier, Random Forest, etc. to obtain a classifier that recognizes new classes of images. In an exemplary configuration of a system and method according to aspects of the invention, all the images from the training and test sets were loaded, and their features extracted using the above pre-trained CNN models. The extracted features were stored keyed on the image id to new files in HDF5 dataset format. Those are later loaded and used as inputs for training with general machine learning classifiers, such as Logistic Regression and SVM and also used as input features for later retrieval purpose.

Finding a unique feature representation to classify or compare images accurately for all types of queries may present a significant challenge. Feature descriptors at different levels of image representation are in diverse forms and may be complementary in nature. Hence, the different features extracted from the pre-trained CNNs in this exemplary configuration were fused together in all possible combinations using the Partial Least Square Canonical Correlation Analysis (CCA). This results in a unique feature vector derived from a correlation analysis of the extracted features with different combinations, such as ResNet-Inception features, Inception-VGG features, ResNet-VGG features, or a combination of all three features as ResNet-Inception-VGG features. The CCA is used in establishing a common structure to describe the multiple collinearity of the features extracted from two CNNs. It maximizes the correlation between the matrix of vectors from one feature database X(p) and a matrix of feature vectors over another database Y(q) in the sense of finding a weighted linear composite that expresses the overlap between distribution X(p) as feature 1 and distribution Y(q) as feature 2:

$X = X_1 \ldots X_p$ and $Y = Y_1 \ldots Y_q$

The goal of canonical correlation is to find linear combinations of X and Y, f(u, v) that maximizes the correlation between X and Y.

$$u = b_1 X_1 \ldots b_p X_p$$

$$v = a_1 Y_1 \ldots a_q Y_q$$

Fused Features = corr(Xu, Yv), where, $$\text{corr}(Xu, Yv) = \frac{u^t X^t Y v}{\sqrt{u^t X^t X u} \sqrt{v^t Y^t Y v}}$$

CCA maximizes corr(Xu, Yv), and u and v are unit vectors ($u \in R^p$, $v \in R^q$). The maximization of corr(Xu, Yv) is also equivalent to the maximization of f(u, v).

corr(Xu, Yv) thus provides a single, combined feature vector that fuses features extracted from the subject image, and thus represents all extracted features in that single feature vector. Such feature extraction process is carried out on both pre-existing images of skin legions whose pathologies had already been established (for purposes of building database 170), and on query images captured by image capture device 200 and transmitted by the medical practitioner to system 100 for analysis and assistance in diagnosing the skin lesion shown in the captured query image. Distance measures are applied to the query features and the features from the database images from database based on the closeness of those features, as discussed in greater detail below.

To implement the feature learning methods, a distributed deep-learning library may be used, which may be written in computer languages such as Python, Java and Scala, and integrated with Hadoop and Spark.

Figure 4:
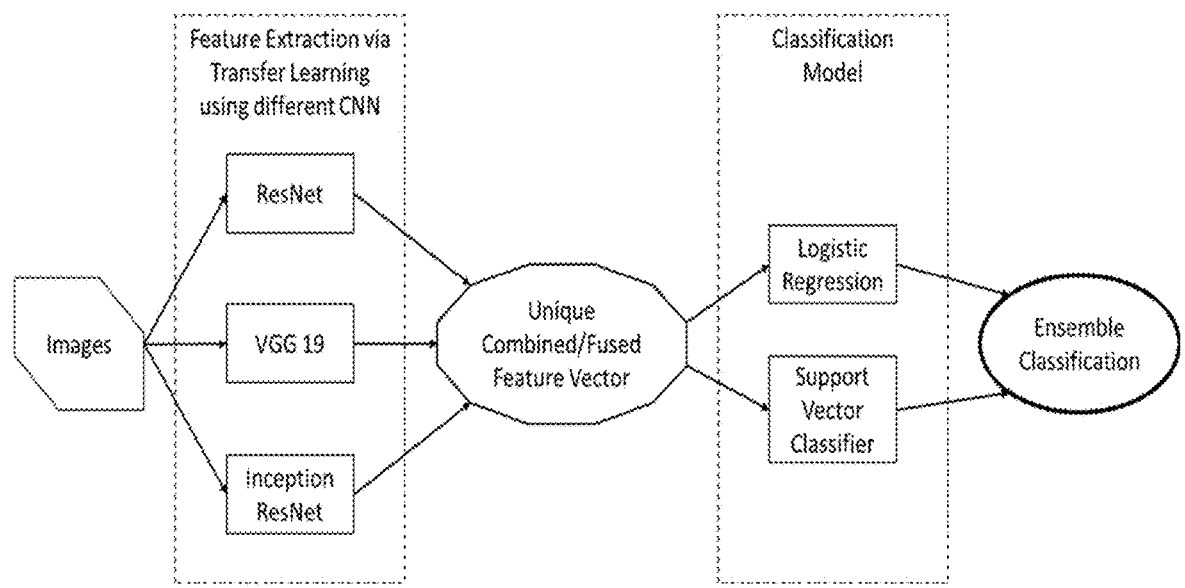
FIG. 4 is a schematic diagram of a feature vector classification process that may be implemented by a classification module of the system of FIG. 1.

Classification module 170 may be used to classify the images in multiple skin cancer categories. In a particular preferred configuration, systems and methods employing aspects of the invention may incorporate an ensemble of classification models, which may include (by way of non-limiting example) a Logistical Regression (LR) model and Support Vector Classifier (SVC) model, each trained on each individual or fused feature vectors with different feature combinations produced by feature extraction module 140, as shown in the schematic view of FIG. 4. Preferably, a user may employ user interface 160 to choose any combination of classifiers for ensemble learning. Ensemble learning involves taking multiple classifiers and aggregating them into a single meta-classifier. By averaging multiple machine learning models together, we may outperform (i.e., achieve higher accuracy) by using just a single model chosen at random. In a particular exemplary configuration, multiple networks were trained and then asked to return the probabilities for each class label given an input data point. Such probabilities are averaged together, and the final classification is obtained. By averaging multiple machine learning models together, higher accuracy may be achieved by using just a single model chosen at random.

Similarity matching is an essential final processing step employed by system 100, and is used to select and display to the medical practitioner via user interface 160 probability classifications for the queried patient image lesion, preferably including a calculated probability of each classification (i.e., cancer type, if any) for the queried image, and preferably including images of the most similar images in database 170 to the queried image (as discussed in greater detail below). For a given query image captured by image capture device 200 and transmitted to system 100, a search is made on the images in database 170 based on the deep features representing each dermoscopic image. The difference between the feature vector of the query image (patient lesion) and the feature vectors of lesions of reference images in database 170 is preferably calculated based on different distance measures, such as Euclidean, Manhattan, and Cosine methods (which methods are known to those skilled in the art) to compute the similarity between the query image and the database. Current CAD schemes using CBIR approaches typically use the k-nearest neighbor type searching method, which involves searching from the k most similar reference ROIs (i.e., lesions) to the queried ROI (i.e., patient lesion). The smaller the difference (i.e., "distance"), the higher the computed "similarity" level is between the two compared ROIs. The searching and retrieval result of the CBIR algorithm depends on the effectiveness of the distance metrics to measure the similarity level among the selected images. Preferably, the query-specific adaptive similarity fusion approach set forth herein effectively exploits the online lesion classification information and adjusts the feature weights accordingly in a dynamic fashion.

Benchmarking is currently performed based on a system that was trained on a test dataset of 1,300 images, but is automated and generalizable to any dataset. This provides a system that allows any dermatologist that has no prior knowledge of deep learning to put in a dataset and generate a system based on that dataset. This is unique as most diagnostic aids work based on the system-provided models. In this way, it is possible to generate a system that can make over a thousand type classifications, if provided with a dataset that has such, and the system becomes generalized to include other medical classifications based on the dataset provided. The technology may accommodate more datasets as needed, on the order of over 100,000 images. The images consist of at least 7 types of skin cancer, but the architecture is designed to classify at least 100 types of skin cancer to include both melanoma and non-melanoma related cancer. Similarity matching is also done based on the dataset provided.

Computer applications employing the foregoing methods may be implemented to enable the diagnosis of possible skin cancer types.

Figure 5:
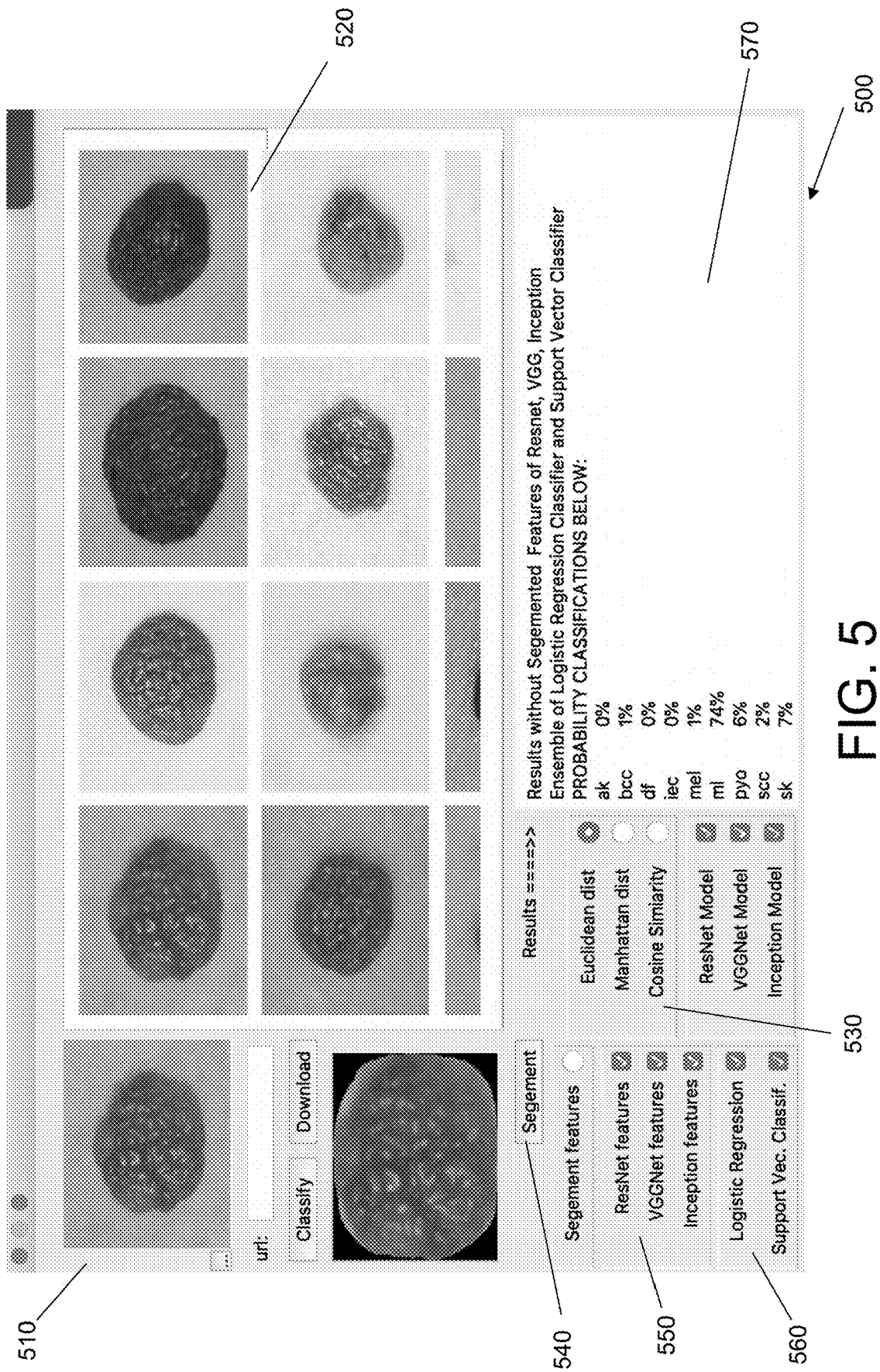
FIG. 5 is an exemplary display presented to a user by a user interface of the system of FIG. 1.

Next, FIG. 5 shows a display that may be presented to a user, such as the medical practitioner that transmitted the query image to system 100, by user interface 160 of system 100. The user interface 500 primarily consists of a query panel 510 to display the query image (which can be selected either from an URL or browsed through a folder), and a display panel 520 to show the most similar images to the query image based on selecting a distance measure 530, such as Euclidean, Manhattan, and Cosine to perform similarity matching. In addition, the interface also provides the options for segmenting at 540 the query image for lesion detection, and also options for selecting different combinations of deep features 550 and classification model 560.

Hence, a combination of CNNs can be selected to fuse features for a query image and a late fusion of classification probabilities can be made with checkbox selections of either Logistic Regression or SVM Classifiers. The classification result as probabilistic outputs of different categories are displayed in Probability Classifications window 570 as percentages. The result varies with the feature and classification selections made as shown in Table 2 above. Overall, the interface presented to the user is very user friendly and flexible for the user where he/she can perform both classification and retrieval by selecting from a number of options.

Experimental Results

In order to evaluate the effectiveness of a system and method configured in accordance with aspects of the invention, experiments implementing the foregoing methods were performed on the Dermofit Image Library, which is a collection of 1,300 high quality dermoscopic images collected under standardized conditions. The lesions shown in those images non-uniformly span across ten different categories as shown in Table 1 below. Each image has a gold standard diagnosis based on expert opinion (including dermatologists and dermatopathologists). A binary segmentation mask that denotes the lesion area.

TABLE 1

Categories of lesions and number of associated images

| Lesion Type | # Images |
|---|---|
| Actinic Keratosis | 45 |
| Basal Cell Carcinoma | 239 |
| Melanocytic Nevus (mole) | 331 |
| Seborrhoeic Keratosis | 257 |
| Squamous Cell Carinoma | 88 |
| Intraepithelial Carcinoma | 78 |
| Pyogenic Granuloma | 24 |
| Haemangioma | 97 |
| Dermatofibroma | 65 |
| Malignant Melanoma | 76 |

To experiment with the classification and retrieval systems, the entire collection of 1300 images is uniformly divided (to keep the class distribution close to the entire data set) where 75% of the images are established as the training set and the remaining 25% as the test set (query images).

The classification accuracy of the system configured in accordance with aspects of the invention is measured with weighted average precision, recall and F1 score. Weighting by class frequency might provide a better estimate of overall performance, since the class frequencies are not uniform in the data set (Table 1). The retrieval effectiveness is measured with the precision-recall (PR) graphs that are commonly used in the information retrieval domain. For the experiments, each image in the testing dataset is served as a query image. A retrieved image is considered to be a correct match if it belongs to the same category to which the query image belongs.

Lesion segmentation training data included the original image, paired with the expert manual tracing of the lesion boundaries in the form of a binary mask, where pixel values of 255 are considered inside the area of the lesion, and pixel values of 0 are outside. The performance of segmentation is measured using the common segmentation metrics, such as pixel-level sensitivity, pixel-level specificity, Dice Coefficient, and Jaccard Index:

$$JA = \frac{TP}{TP + FN + FP}$$

where TP, TN, FP, and FN refer to true positive, true negative, false positive, and false negative, at the pixel level, respectively. Pixel values above 128 were considered positive, and pixel values below were considered negative. For lesion segmentation based on U-Net, a Jaccard index of 0.84, a Dice index of 0.73, a specificity of 0.83 and a Sensitivity of 0.90 were achieved. For example, Jaccard index gives a measure of the overlap between the ground truth and the system segmentation.

Table 2 shows the classification performance of the system configured as discussed above by means of weighted average precision, recall, and F1 scores. It is observed that the best performance in terms of precision (0.85), recall (0.85), and F1 score (0.84) is achieved by using the ensemble classification on the combined/fused feature vector from all three pre-trained CNNs (i.e., ResNet, VGG, and Inception). This justifies the use of the foregoing ensemble method of averaging multiple machine learning models together by fusing all available features instead of using a single model. The empirical results also indicate that the foregoing approach achieves comparable performance in comparison to other related research reported in the literature.

TABLE 2

Classification performances

| Fused Features | Classifier | Weighted Avg Precision | Weighted Avg Recall | Weighted Avg F1-Score |
|---|---|---|---|---|
| ResNet, VGG and Inception | LR | 0.83 | 0.81 | 0.80 |
| | SVC | 0.80 | 0.79 | 0.79 |
| | Ensemble LR and SVC | 0.85 | 0.85 | 0.84 |
| Inception | LR | 0.71 | 0.70 | 0.69 |
| | SVC | 0.67 | 0.66 | 0.65 |
| | Ensemble LR and SVC | 0.69 | 0.68 | 0.67 |
| ResNet | LR | 0.80 | 0.80 | 0.80 |
| | SVC | 0.81 | 0.81 | 0.81 |
| | Ensemble LR and SVC | 0.81 | 0.81 | 0.80 |
| VGG | LR | 0.72 | 0.72 | 0.72 |
| | SVC | 0.70 | 0.69 | 0.69 |
| | Ensemble LR and SVC | 0.72 | 0.72 | 0.71 |
| ResNet and Inception | LR | 0.76 | 0.76 | 0.75 |
| | SVC | 0.78 | 0.77 | 0.77 |
| | Ensemble LR and SVC | 0.77 | 0.76 | 0.76 |
| ResNet and VGG | LR | 0.76 | 0.76 | 0.76 |
| | SVC | 0.76 | 0.75 | 0.75 |
| | Ensemble LR and SVC | 0.76 | 0.76 | 0.75 |
| VGG and Inception | LR | 0.70 | 0.69 | 0.69 |
| | SVC | 0.71 | 0.70 | 0.70 |
| | Ensemble LR and SVC | 0.70 | 0.70 | 0.70 |

To find a suitable similarity matching function, performances of the three distance measures, such as the Euclidean, Cosine, and Manhattan, are compared on ResNet extracted feature space by using only 20 query image features in the test set. ResNet was chosen since it gave the highest individual classification accuracies as shown in Table 2.

Analysis of the results of such comparison showed that the Euclidean distance measure easily outperformed the other two distance measures in terms of precision at each of the recall points. Hence, for further analysis, only the Euclidean measure was used for similarity matching in database images.

The average Precision-Recall (PR) curves of seven different combinations of individual and fused features for query images in the test set based on applying Euclidean distance measure only were generated and compared. The retrieval results also indicate the same level of performance when compared to the classification performance in Table 1 above for different combinations, and the highest performance is achieved by fusing all three features together (i.e., ResNet-Inception-VGG features).

Figure 6:
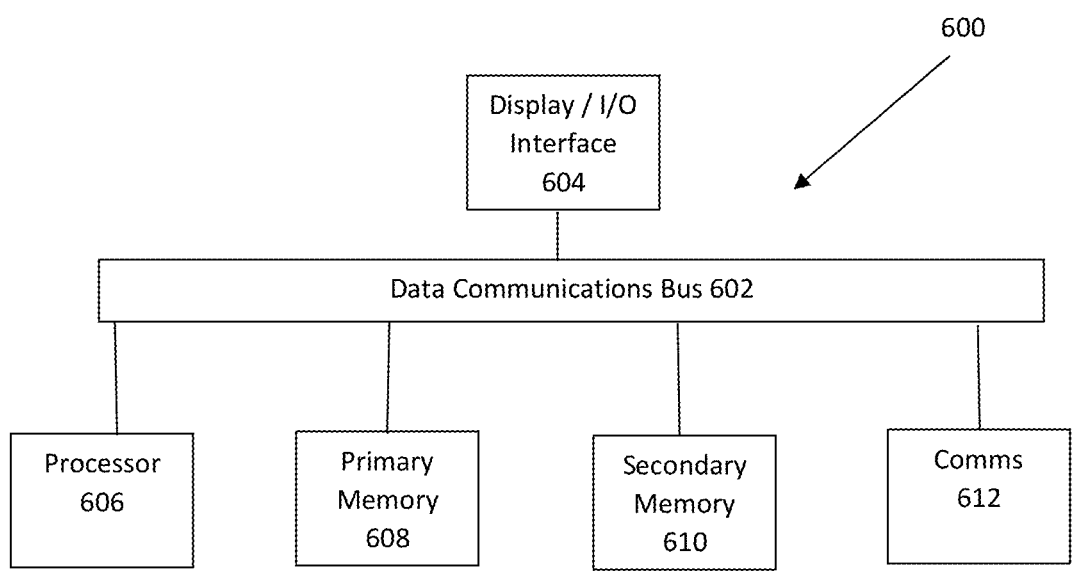
FIG. 6 is a schematic view of an exemplary computer system suitable for implementing the methods described herein.

Next, FIG. 6 shows an exemplary computer system 600 suitable for implementing the methods described herein. Those skilled in the art will recognize that system 100 for aiding in the diagnosis of a skin lesion through digital image processing may take the form of computer system 600 as reflected in FIG. 6, though variations thereof may readily be implemented by persons skilled in the art as may be desirable for any particular installation. In each such case, one or more computer systems 600 may carry out the foregoing methods as computer code.

Computer system 600 includes a communications bus 602, or other communications infrastructure, which communicates data to other elements of computer system 600. For example, communications bus 602 may communicate data (e.g., text, graphics, video, other data) between bus 602 and an I/O interface 604, which may include a display, a data entry device such as a keyboard, touch screen, mouse, or the like, and any other peripheral devices capable of entering and/or viewing data as may be apparent to those skilled in the art. Further, computer system 600 includes a processor 606, which may comprise a special purpose or a general purpose digital signal processor. Still further, computer system 600 includes a primary memory 608, which may include by way of non-limiting example random access memory ("RAM"), read-only memory ("ROM"), one or more mass storage devices, or any combination of tangible, non-transitory memory. Still further, computer system 600 includes a secondary memory 610, which may comprise a hard disk, a removable data storage unit, or any combination of tangible, non-transitory memory. Finally, computer system 600 may include a communications interface 612, such as a modem, a network interface (e.g., an Ethernet card or cable), a communications port, a PCMCIA slot and card, a wired or wireless communications system (such as Wi-Fi, Bluetooth, Infrared, and the like), local area networks, wide area networks, intranets, and the like.

Each of primary memory 608, secondary memory 610, communications interface 612, and combinations of the foregoing may function as a computer usable storage medium or computer readable storage medium to store and/or access computer software including computer instructions. For example, computer programs or other instructions may be loaded into the computer system 600 such as through a removable data storage device (e.g., a floppy disk, ZIP disks, magnetic tape, portable flash drive, optical disk such as a CD, DVD, or Blu-ray disk, Micro Electro Mechanical Systems ("MEMS"), and the like). Thus, computer software including computer instructions may be transferred from, e.g., a removable storage or hard disc to secondary memory 610, or through data communication bus 602 to primary memory 608.

Communication interface 612 allows software, instructions and data to be transferred between the computer system 600 and external devices or external networks. Software, instructions, and/or data transferred by the communication interface 612 are typically in the form of signals that may be electronic, electromagnetic, optical or other signals capable of being sent and received by communication interface 612. Signals may be sent and received using a cable or wire, fiber optics, telephone line, cellular telephone connection, radio frequency ("RF") communication, wireless communication, or other communication channels as will occur to those of ordinary skill in the art.

Computer programs, when executed, allow the processor of computer system 600 to implement the methods discussed herein for the automated diagnoses of a skin cancer type from a dermoscopic image, according to computer software including instructions.

Computer system 600 may perform any one of, or any combination of, the steps of any of the methods described herein. It is also contemplated that the methods according to the present invention may be performed automatically, or may be accomplished by some form of manual intervention.

The computer system 600 of FIG. 6 is provided only for purposes of illustration, such that the invention is not limited to this specific embodiment. Persons having ordinary skill in the art are capable of programming and implementing the instant invention using any computer system.

Further, computer system 600 may, in certain implementations, comprise a handheld device and may include any small-sized computing device, including by way of non-limiting example a cellular telephone, a smartphone or other smart handheld computing device, a personal digital assistant, a laptop or notebook computer, a tablet computer, a hand held console, an MP3 player, or other similarly configured small-size, portable computing device as may occur to those skilled in the art.

The system of FIG. 1 may, in an exemplary configuration, be implemented in a cloud computing environment for carrying out the methods described herein. That cloud computing environment uses the resources from various networks as a collective virtual computer, where the services and applications can run independently from a particular computer or server configuration making hardware less important. The cloud computer environment includes at least one user computing device. The client computer may be any device that may be used to access a distributed computing environment to perform the methods disclosed herein, and may include (by way of non-limiting example) a desktop computer, a portable computer, a mobile phone, a personal digital assistant, a tablet computer, or any similarly configured computing device.

A client computer preferably includes memory such as RAM, ROM, one or more mass storage devices, or any combination of the foregoing. The memory functions as a computer readable storage medium to store and/or access computer software and/or instructions.

A client computer also preferably includes a communications interface, such as a modem, a network interface (e.g., an Ethernet card), a communications port, a PCMCIA slot and card, wired or wireless systems, and the like. The communications interface allows communication through transferred signals between the client computer and external devices including networks such as the Internet and a cloud data center. Communication may be implemented using wireless or wired capability, including (by way of non-limiting example) cable, fiber optics, telephone line, cellular telephone, radio waves or other communications channels as may occur to those skilled in the art.

Such client computer establishes communication with the one or more servers via, for example, the Internet, to in turn establish communication with one or more cloud data centers that implement diagnosing system 100. A cloud data center may include one or more networks that are managed through a cloud management system. Each such network includes resource servers that permit access to a collection of computing resources and components of diagnosing system 100, which computing resources and components can be invoked to instantiate a virtual computer, process, or other resource for a limited or defined duration. For example, one group of resource servers can host and serve an operating system or components thereof to deliver and instantiate a virtual computer. Another group of resource servers can accept requests to host computing cycles or processor time, to supply a defined level of processing power for a virtual computer. Another group of resource servers can host and serve applications to load on an instantiation of a virtual computer, such as an email client, a browser application, a messaging application, or other applications or software.

The cloud management system may comprise a dedicated or centralized server and/or other software, hardware, and network tools to communicate with one or more networks, such as the Internet or other public or private network, and their associated sets of resource servers. The cloud management system may be configured to query and identify the computing resources and components managed by the set of resource servers needed and available for use in the cloud data center. More particularly, the cloud management system may be configured to identify the hardware resources and components such as type and amount of processing power, type and amount of memory, type and amount of storage, type and amount of network bandwidth and the like, of the set of resource servers needed and available for use in the cloud data center. The cloud management system can also be configured to identify the software resources and components, such as type of operating system, application programs, etc., of the set of resource servers needed and available for use in the cloud data center.

In accordance with still further aspects of an embodiment of the invention, a computer program product may be provided to provide software to the cloud computing environment. Computer products store software on any computer useable medium, known now or in the future. Such software, when executed, may implement the methods according to certain embodiments of the invention. By way of non-limiting example, such computer usable mediums may include primary storage devices (e.g., any type of random access memory), secondary storage devices (e.g., hard drives, floppy disks, CD ROMS, ZIP disks, tapes, magnetic storage devices, optical storage devices, MEMS, nanotech storage devices, etc.), and communication mediums (e.g., wired and wireless communications networks, local area networks, wide area networks, intranets, etc.). Those skilled in the art will recognize that the embodiments described herein may be implemented using software, hardware, firmware, or combinations thereof.

The cloud computing environment described above is provided only for purposes of illustration and does not limit the invention to this specific embodiment. It will be appreciated that those skilled in the art are readily able to program and implement the invention using any computer system or network architecture.

Thus and in accordance with all of the foregoing, an integrated decision support system may be provided for the automatic skin cancer recognition of pigmented skin lesions. It is hypothesized that such an integrated system would greatly improve the decision making process for both novice and expert dermatologists for early cancer screening. The system is evaluated for the retrieval and classification of the dermoscopic images in a dataset of ten different cancer categories. The experimental results indicate that the approach is effective to retrieve visually similar lesions from a database and to predict the categories of images for diagnostic correctness. Image retrieval and ensemble-based decision making can be integrated and interactively utilized as a diagnostic support tool to help the dermatologist for skin cancer recognition. However, it is recognized that many other advanced image-based features, and features from other sources, would be helpful for a complete DSS for real clinical integration. Nonetheless, the presence of an expert dermatologist is still considered most preferably for the overall visual assessment of the skin lesion and the final diagnosis, based on the objective evaluation suggested by the system and contextual information from the patient data.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. For example, while the exemplary case discussed above describes an analysis that is undertaken with respect to a single intersection, the system may readily be implemented to similarly adapt the ideal speed profile for a series of more than one signalized intersections, and continuously report the recommended speed to the user as discussed above. Similarly, the systems and methods described herein may be used in simulated driving environments for a wide variety of simulated road vehicles, including by way of non-limiting example in simulated cars, trucks, buses, and the like. It should be understood, therefore, that the invention may be practiced otherwise than as specifically set forth herein.

What is claimed is:

1. An automated method for diagnosing a skin cancer type from a dermoscopic image, comprising:
   receiving at a processor of a diagnosing system computer a digital query image of a skin lesion from an image capture device;
   comparing at said processor said digital query image to a plurality of digital images in a database, wherein said database comprises digital images of pathologically confirmed types of skin lesions;
   selecting at said processor a plurality of said pathologically confirmed digital images from said database that have a designated similarity to said digital query image; and
   causing said processor to display to a user probabilities that said digital query image displays a skin lesion having a pathology matching each of a plurality of skin cancer types.

2. The automated method for diagnosing a skin cancer type of claim 1, further comprising the step of causing said processor to display said plurality of pathologically confirmed digital images to said user.

3. The automated method for diagnosing a skin cancer type of claim 1, wherein said comparing step further comprises applying at said processor a deep feature extraction to said digital query image to generate a feature vector quantifying contents of the digital query image.

4. The automated method for diagnosing a skin cancer type of claim 3, wherein said step of applying a deep feature extraction to said digital query image further comprises using at said processor a plurality of pretrained Convolutional Neural Networks feature vectors to generate a combined feature vector.

5. The automated method for diagnosing a skin cancer type of claim 3, wherein said comparing step further comprises applying at said processor a classification to said feature vector as one of multiple types of skin cancer.

6. The automated method for diagnosing a skin cancer type of claim 5, wherein applying a classification to said feature vector further comprising using both Logistical Regression and Support Vector Classifier processes.

7. The automated method for diagnosing a skin cancer type of claim 1, further comprising the step of causing said processor to select said plurality of said pathologically confirmed digital images based on a distance measure between a feature vector of said digital query image and said plurality of pathologically confirmed digital images.

8. The automated method for diagnosing a skin cancer type of claim 1, further comprising the step of:
   prior to said comparing step, segmenting said digital query image to delineate boundaries of a lesion displayed in said digital query image.

9. A system for the automated diagnosing of a skin cancer type from a dermoscopic image, comprising a memory and a processor in data communication with said memory, the memory having computer executable instructions stored thereon configured to be executed by the processor to cause the system to:
   receive a digital query image of a skin lesion from an image capture device;
   compare at said processor said digital query image to a plurality of digital images in a database, wherein said database comprises digital images of pathologically confirmed types of skin lesions;
   select a plurality of said pathologically confirmed digital images from said database that have a designated similarity to said digital query image; and
   display to a user probabilities that said digital query image displays a skin lesion having a pathology matching each of a plurality of skin cancer types.

10. The system for the automated diagnosing of a skin cancer type of claim 9, wherein said computer executable instructions are further configured to cause said processor to display said plurality of pathologically confirmed digital images to said user.

11. The system for the automated diagnosing a skin cancer type of claim 9, wherein said computer executable instructions configured to compare said digital query image to the plurality of digital images are further configured to apply a deep feature extraction to said digital query image to generate a feature vector quantifying contents of the digital query image.

12. The system for the automated diagnosing of a skin cancer type of claim 11, wherein said computer executable instructions configured to apply a deep feature extraction to said digital query image are further configured to use a plurality of pretrained Convolutional Neural Networks feature vectors to generate a combined feature vector.

13. The system for the automated diagnosing of a skin cancer type of claim 11, wherein said computer executable instructions configured to compare said digital query image to the plurality of digital images are further configured to apply a classification to said feature vector as one of multiple types of skin cancer.

14. The system for the automated diagnosing of a skin cancer type of claim 13, wherein said computer executable instructions configured to apply a classification to said feature vector are further configured to use both Logistical Regression and Support Vector Classifier processes.

15. The system for the automated diagnosing of a skin cancer type of claim 9, wherein said computer executable instructions are further configured to select said plurality of said pathologically confirmed digital images based on a distance measure between a feature vector of said digital query image and said plurality of pathologically confirmed digital images.

16. The system for the automated diagnosing of a skin cancer type of claim 9, wherein said computer executable instructions are further configured to:
   prior to comparing said digital query image to the plurality of digital images, segment said digital query image to delineate boundaries of a lesion displayed in said digital query image.

17. A non-transitory computer-readable medium having stored thereon one or more code sections each comprising a plurality of instructions executable by one or more processors, the instructions configured to cause the one or more processors to perform the actions of an automated method for diagnosing a skin cancer type, the actions of the method comprising the steps of:
   receiving a digital query image of a skin lesion from an image capture device;
   comparing said digital query image to a plurality of digital images in a database, wherein said database comprises digital images of pathologically confirmed types of skin lesions;
   selecting a plurality of said pathologically confirmed digital images from said database that have a designated similarity to said digital query image; and
   displaying to a user probabilities that said digital query image displays a skin lesion having a pathology matching each of a plurality of skin cancer types.

18. The non-transitory computer-readable medium of claim 17, the method further comprising the step of causing said processor to display said plurality of pathologically confirmed digital images to said user.

19. The non-transitory computer-readable medium of claim 17, the method further comprising the step of selecting said plurality of said pathologically confirmed digital images based on a distance measure between a feature vector of said digital query image and said plurality of pathologically confirmed digital images.

20. The non-transitory computer-readable medium of claim 17, the method further comprising the step of:
   segment said digital query image to delineate boundaries of a lesion displayed in said digital query image.

* * * * *